United States Patent [19]
Markle et al.

[11] Patent Number: 5,354,448
[45] Date of Patent: * Oct. 11, 1994

[54] ELECTROCHEMICAL SENSOR

[75] Inventors: David R. Markle, Paoli; Stuart P. Hendry, Aylesbury, England

[73] Assignee: Biomedical Sensors Ltd., High Wycombe, England

[ * ] Notice: The portion of the term of this patent subsequent to Nov. 16, 2010 has been disclaimed.

[21] Appl. No.: 95,232

[22] Filed: Jul. 20, 1993

Related U.S. Application Data

[63] Continuation-in-part of Ser. No. 887,615, May 22, 1992, Pat. No. 5,262,037.

[51] Int. Cl.$^5$ .............................. G01N 27/26
[52] U.S. Cl. .................. 204/415; 204/403; 128/635
[58] Field of Search ............... 204/415, 403; 128/635, 128/637, 639, 657, 658

[56] References Cited

U.S. PATENT DOCUMENTS 3,905,888  9/1975  Mindt et al. ............. 204/415
5,262,037 11/1993  Markle et al. ............ 204/403

Primary Examiner—John Niebling
Assistant Examiner—Bruce F. Bell
Attorney, Agent, or Firm—Peter C. Richardson; Lawrence C. Akers; Mark Dryer

[57] ABSTRACT

An electrochemical sensor for the determination of the partial pressure of oxygen in a bloodstream comprising a cathode and an anode immersed in an electrolyte contained in a chamber defined by an oxygen gas permeable membrane wherein the insulated portion of each of the conductors forming the cathode and the anode has an additional layer of insulation applied over the original insulation.

7 Claims, 2 Drawing Sheets

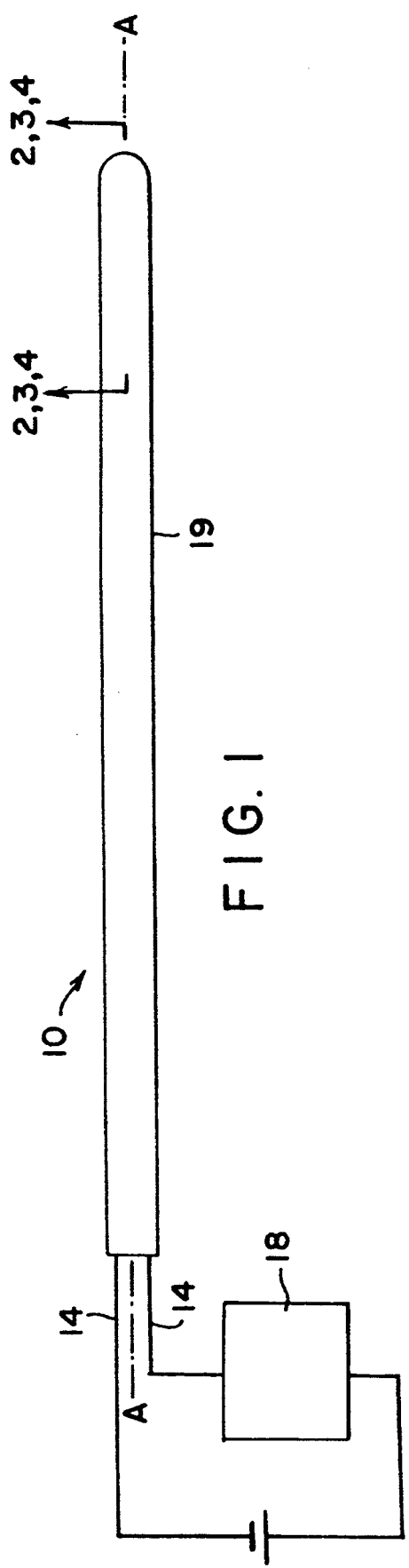
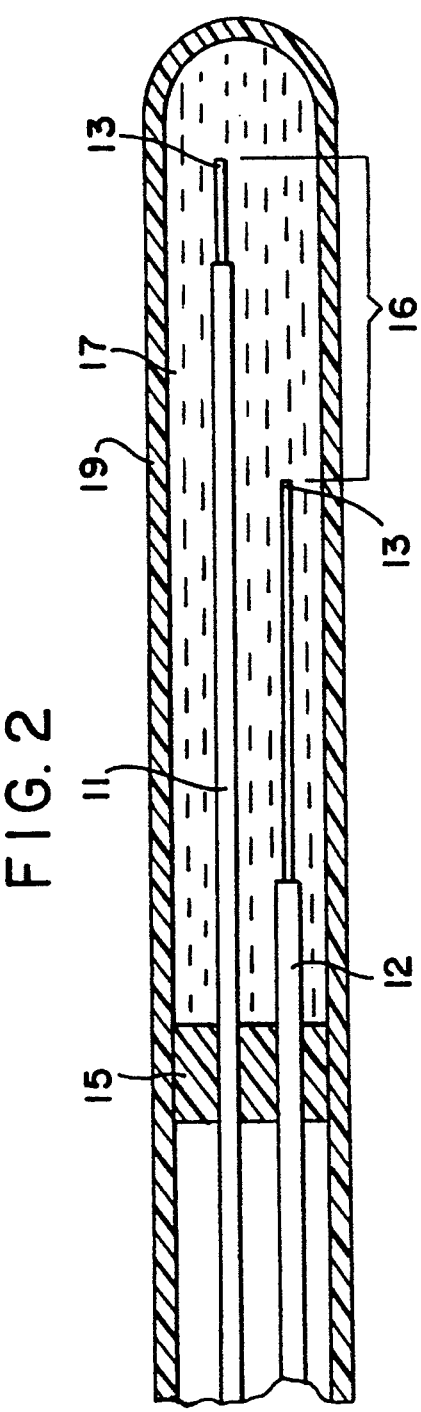
FIG. 1
FIG. 2

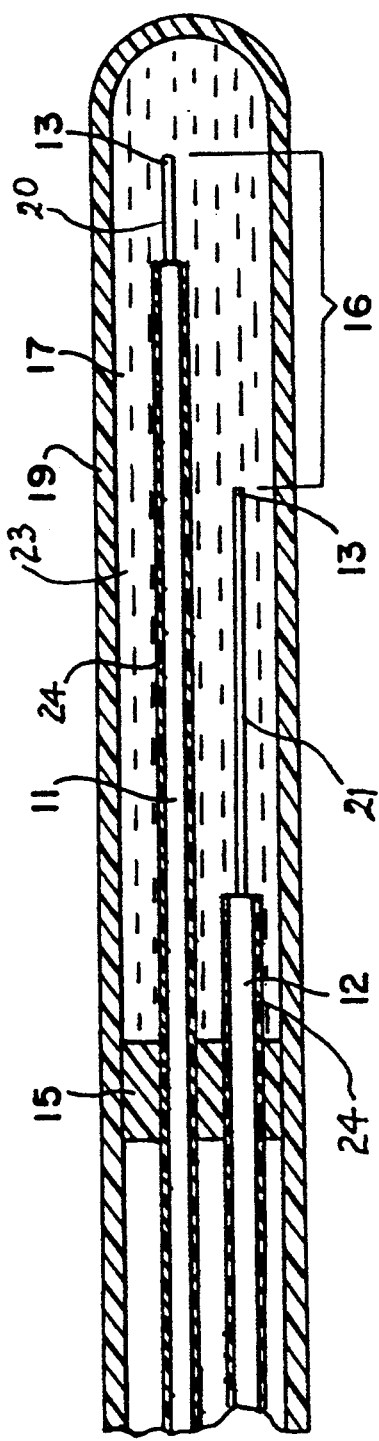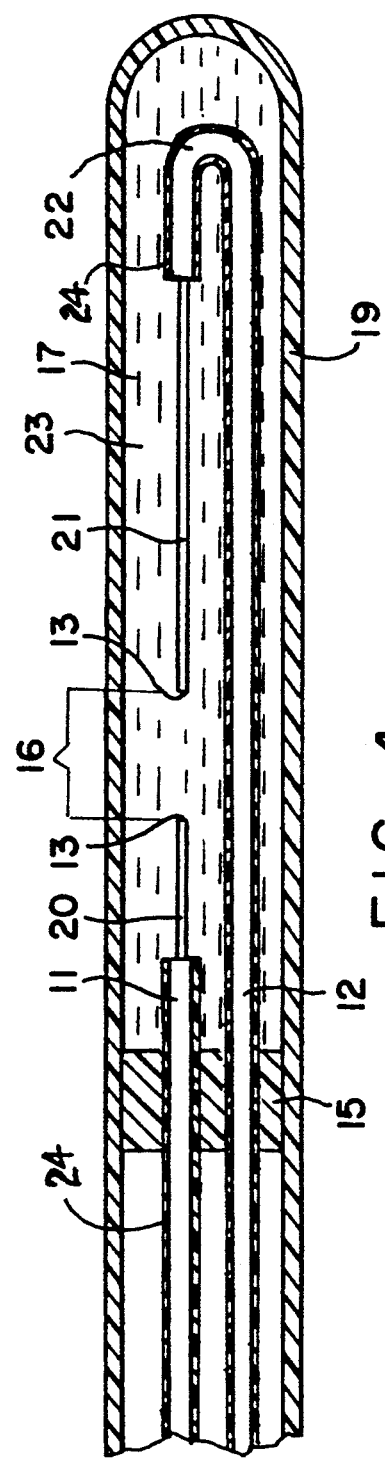

ELECTROCHEMICAL SENSOR

BACKGROUND OF THE INVENTION

This is a continuation in part of U.S. patent application Ser. No. 07/877,615 filed May 22, 1992, (now U.S. Pat. No. 5,262,037). The present invention relates to an electrochemical sensor having improved insulation which eliminates electrical shorting.

U.S. Pat. No. 3,905,888 discloses an electrochemical sensor for determining the oxygen partial pressure, particularly in biological media in vivo. The sensor has two electrodes disposed in a chamber which contains an electrolyte and the walls of which are permeable to oxygen. The electrodes comprise a pair of wires of different lengths parallel to the longitudinal axis of the chamber. The longer wire has an insulating layer in the region over which the shorter wire extends, the active surfaces of the electrodes being formed by the non-insulated exposed surfaces of the wire ends. Typically the electrode with the longer active surface is the anode and the wire is preferably made of silver. The electrode with the shorter active surface is the cathode and the wire is preferably made of platinum or, alternatively, silver.

If holes exist in the insulation of the cathode dendrites will grow through the hole to the anode and short out the sensor. To avoid that problem the length over which an uninsulated portion is next to an insulated part is minimized. That geometric arrangement also is prone to failure because the metal consumed tends to be at the base of the anode near the distal end of the insulation, which is the site for the shortest path for flow of current between the anode and the cathode. After a while the anode becomes separated from its insulated base when the silver thereat has been consumed.

A longer lived and more reliable structure for the conductors in an electrochemical sensor is described and claimed in U.S. Pat. No. 5,262,037 which provides an electrochemical sensor for the determination of the partial pressure of oxygen in a blood stream comprising a cathode and an anode immersed in an electrolyte contained in a chamber defined by an oxygen gas permeable membrane, wherein each of the cathode and anode comprises the exposed uninsulated distal portion of a plurality of elongate insulated conductors each having an exposed uninsulated distal end surface and a proximal end; the elongate insulated conductors being associated with a support which positions each conductor with the insulated portions in parallel and the elongate conductor or conductors which form the anode is folded into a "U" shape so that the exposed distal end surface thereof faces the distal end surface of the cathode; the gap between the facing distal end surfaces of the cathode and anode being filled with an electrolyte to permit the flow of electric current across the gap; and the proximal end of each of the conductors is adapted to be connected to a current sensitive measuring device in circuit with a power source for monitoring changes in the flow of electric current between the distal end surfaces.

In the above-described sensor of U.S. patent application Ser. No. 5,262,037 the configuration of the anode and cathode overcomes the aforementioned deficiencies in the sensor disclosed in U.S. Pat. No. 3,905,888. Surprisingly, it has now been found that a $pO_2$ sensor, such as that disclosed in U.S. Pat. No. 3,905,880, may be improved, and the sensor disclosed in Patent Application Serial No. 07/887,617 may be further improved, by using a single conductor for each of the anode and cathode and increasing the insulation on the insulated conductors which terminate in the exposed anode and cathode in the manner disclosed herein. The improvement is surprising because, although a post facto judgment might suggest additional insulation to prevent short circuiting, it has been found that merely adding layers of the same insulation does not solve the problem; and moreover the insulation was subject to damage during ordinary manufacture handling.

SUMMARY OF THE INVENTION

In accordance with the present invention there is provided an electrochemical sensor for the determination of the partial pressure of oxygen in a blood stream comprising a cathode and an anode immersed in an electrolyte contained in a chamber defined by an oxygen gas permeable membrane, wherein each of the cathode and anode comprises an exposed, uninsulated distal portion of an elongated insulated conductor having an exposed uninsulated distal end surface and a proximal end; the elongated insulated conductors being associated with a support which positions each conductor with the insulated portion in parallel; and wherein the insulated portion of each conductor has an additional layer of insulation applied over the original insulation.

Preferably the cathode is made from silver and the anode is made from silver or silver chloride. Alternatively, one or both of the electrodes may be made from platinum.

The gap between the anode and cathode is filled with an electrolyte, preferably a buffered potassium chloride solution, which permits flow of electric current across the gap and between the distal end surfaces.

DETAILED DESCRIPTION OF THE INVENTION

The sensor of the invention preferably forms part of an electrical circuit for the in vivo monitoring of the partial pressure of oxygen in a patient's blood stream. Such a circuit comprises, in combination, an electrochemical sensor as described above connected, through the proximal end of each of the conductors to a current sensitive measuring device in circuit with a power source, whereby changes in the flow of electrical current between the anode and cathode may be monitored.

An electrochemical cell preferably results from the conductors, the electrolyte in the gap and the current sensitive measuring device in circuit with a power source. The electrochemical cell is an oxygen sensitive device generating a current flow between one conductor, that is an anode and another conductor, that is a cathode. The current is measurable at the proximal ends.

The electrolyte is contained within a gas permeable membrane that permits oxygen to diffuse therethrough and the cathode is an insulated metal, preferably silver, wire and the anode is an insulated silver and/or silver chloride wire. Each wire is stripped of insulation near its respective distal end surface. The membrane is preferably sized to fit within a catheter of a diameter and length sized to be inserted within the vasculature of a human or animal. Preferably, the stripped cathode has a shorter length than the length of the stripped anode.

In the sensor described and claimed in U.S. patent application Ser. No. 07/887,617, the elongate anode is supported parallel to the elongate cathode and the anode is folded near the transition between the stripped portion and insulated part. There the anode is folded into a "U" shape such that the distal end surface thereof faces the distal end surface of the cathode. The sensor resulting from this configuration is an improvement over the sensor disclosed in U.S. Pat. No. 3,905,880.

However, a problem may still arise from short circuiting between the insulated portions of the conductors, due to pin-holes or tears in the insulation which is in contact with the electrolyte.

This problem has now been overcome by the improved sensor of the present invention wherein the insulated portion of the conductors has an additional layer of insulation applied over the original insulation, preferably by co-extrusion.

Prior art electrochemical sensors, such as the sensor disclosed in U.S. Pat. No. 3,905,880, were found to exhibit problems which gave rise to inconsistent readings or complete malfunction and at least one of the problems was solved by the configuration of the electrodes used in the sensor of U.S. Pat. No. 5,262,037. However, when the latter sensors used conductors having the standard insulation used in the art, typically a coating of shellac or the like, which was also the same insulated conductor as that used in the sensors of U.S. Pat. No. 3,905,880, further investigation showed that malfunction of the sensor was due to short-circuiting across the electrolyte arising from tiny holes or tears in the insulation. These flaws in the insulation were due either to imperfections in the manufacturing process itself, usually solvent dipping, or to damage sustained by handling during the manufacture. Although the imperfections in the insulation might be almost microscopic the deleterious effect thereof was quite significant due to the small dimensions of the sensor itself. Once the problem was recognized, it might seem, with hindsight, that increasing the thickness of the insulation would provide a solution. However, merely increasing the original insulation by multiple dips only resulted in an onion skin structure which still contained flaws and was subject to the same tendency to be damaged during normal manufacture handling. Thus the eventual solution (an overlay of insulation according to the present invention) was surprising. Also, because of the small diameter size of the conductors, without or with insulation, and the critical overall size of the completed sensor, special care had to be taken not to overdo the added insulation so as to result in a sensor with an impractical overall diameter. Careful experimentation established that optimum results were obtained by co-extruding a standard insulated conductor, produced by solvent dipping a metal wire in, for example, an alcohol solution of shellac, with an overcoat of a suitable polymer. A preferred insulated conductor is produced by co-extruding an insulated silver wire having a diameter of 0.002 inch with an overcoat of a molten polymer at a temperature of about 300° –500° C. at a rate of about 100–300 feet per minute.

BRIEF DESCRIPTION OF DRAWINGS

The invention will be more particularly described with reference to preferred embodiments illustrated in the accompanying drawings, in which:

FIG. 1 is a perspective and schematic view of an electrical circuit;

FIG. 2 is an enlarged side view in (partial) cross section of a prior art oxygen sensor such as in FIG. 1 as would be seen if the cross section were taken along line 2—2 in FIG. 1. The sensor in FIG. 2 is like that disclosed in U.S. Pat. No. 3,905,888;

FIG. 3 is an enlarged side view in (partial) cross section of an oxygen sensor, such as in FIG. 1 as would be seen if the cross section were taken along line 3—3 in FIG. 1. The conductors of the sensor in FIG. 3 have an additional layer of insulation in accordance with the present invention.

FIG. 4 is an enlarged side view in (partial) cross section of an oxygen sensor, such as in FIG. 1, but as would be seen if the cross section were taken along line 4—4 in FIG. 1. The sensor in FIG. 4 includes the improved arrangement for the cathode and anode as disclosed in U.S. Pat. No. 5,262,037 as well as the additional layer of insulation according to the present invention.

FIG. 1 of the drawings illustrates, in schematic form, an electrical circuit 10 comprising a closed chamber defined by a gas permeable membrane 19 which contains two elongate insulated conductors (see FIGS. 2–4) having proximal ends 14 connected to a current measuring device 18 in circuit with a power source.

The closed chamber of the electrical circuit 10 in a preferred embodiment comprises an electrochemical sensor for placement in the vasculature of a human or animal and so is of a diameter sufficiently small so as to be accommodated within a catheter sized to be inserted in a blood vessel, such as an artery.

As shown in FIGS. 2, 3 and 4, the electrochemical sensor comprises two elongate insulated conductors 11 and 12 each having an exposed uninsulated distal end surface 13 and a proximal end 14 (FIG. 1). The conductors, 11 and 12 are, in the preferred embodiments of FIG. 3 and FIG. 4, thin wires made of silver for the cathode 20 and silver or silver chloride for the anode 21. The preferred embodiment is designed to measure the partial pressure of oxygen entrained in the blood stream.

The distal end surface 13 of each conductor 11 or 12 is preferably substantially normal to its elongate insulated conductor wire. A support 15 associated with the plurality of elongate insulated conductors 11 or 12 positions each conductor 11 or 12 with its uninsulated distal end surface 13 in generally facing relation to the distal end surfaces 13 of one or more other elongate insulated conductors 11 or 12.

A gap 16 between the facing distal end surfaces 13 of the elongate insulated conductor wires defines approximately equal distances between the facing distal end surfaces. An electrolyte 17 is disposed within the gap 16 so that the electrochemistry permits flow of electric current across the gap 16 and between the distal end surfaces 13 as a function of the amount of in vivo entrained gas, i.e. oxygen. The electrolyte 17 preferably is a buffered potassium chloride solution. A current sensitive measuring device 18 in circuit with a power source as shown in FIG. 1, for example, an ampere meter and a battery, is connected to the proximal ends 14 of the elongate insulated conductors 11 and 12. Specifically, the proximal end of the anode connects to the positive terminal of the battery in a manner well known. The ampere meter thus monitors changes in the flow of current through the electrolyte 17 between the distal end surfaces 13.

The preferred embodiment of the electrical circuit 10 has two conductors 11 and 12 as shown in FIGS. 3, and 4. The facing distal end surfaces 13 are substantially parallel to each other. Although parallel facing ends are not essential, the ends should be adjacent to one another so that an electrochemical cell therebetween consumes the uninsulated wire thereof only from the distal end toward the proximal end. That was not the case in the known gas sensors.

Additionally, to prevent short-circuiting between the insulated portions of the conductors and provide a further improvement over the prior art sensors, the insulated portions of the conductors in the sensors of FIG. 3 and FIG. 4 have an additional layer of insulation 24. In the standard insulated wire, such as that illustrated for comparison in FIG. 2, the layer of insulation, for example polyester or shellac, is coated on the metal wire by solvent dipping. The additional layer of insulation in accordance with the present invention is preferably provided by co-extruding the standard insulated wire with an overcoat of insulating polymer, preferably polyester or polyethylene. The temperature for the co-extrusion will depend upon the exact nature of the polymer used for the coating but will generally be in the range of about 300°–500° C. A preferred rate for the extrusion is about 100 to 300 ft. per minute. The preferred conductor is silver wire having a diameter of 0.002 inch.

In particularly preferred embodiment, the dimensions of the conductors as illustrated in FIG. 3 are; for the exposed conductor forming the cathode 20, 0.25 mm; for the exposed conductor forming the anode 21, 10 mm. and for the gap 16, 2.25 mm. This means that the length of insulated conductor 11 facing and parallel to the active surface portion of the anode 21 is 12 mm. Extensive tests have shown that no shorting occurs across the gap defined by this length. Furthermore, there was no shorting between the insulated portions surrounded by the electrolyte. These test represent a significant improvement over prior art sensors, for example the sensor illustrated in FIG. 2.

To achieve the full improvement provided by the present invention it is essential that the additional layer of insulation covers at least that portion of the basic insulation which is in contact with the electrolyte. Additionally it is advantageous if the additional layer of insulation extends the full length of the conductor back to the patient, because of possible tracking or back-up of liquid electrolyte beyond the normal confines of the sensor, i.e. compartment 23 described below.

To separate the cell from the blood stream while permitting measurement of in vivo gas the electrolyte 17 is contained within a compartment 23 defined by an oxygen gas permeable membrane 19 that permits oxygen to diffuse therethrough. In the preferred embodiments of FIG. 3 and FIG. 4, the conductor 11 is an insulated silver wire and the cathode 20 is an exposed distal portion thereof. The conductor 12 is an insulated silver or silver chloride wire and the anode 21 is an exposed distal portion thereof. Each of the cathode and anode terminates in an exposed distal end surface 13. The gas permeable membrane 19 is sized to fit within a catheter (not shown) of a diameter and length sized to be inserted into the vasculature of a human or animal.

An electrochemical cell results from the conductor wires, the electrolyte 17 in the gap 16 and the current sensitive measuring device 18 in circuit with a power source such as a battery between the proximal ends 14. The electrochemical cell is an oxygen sensitive device generating a current flow between one conductor wire, that is the anode 21 and another conductor wire, that is the cathode 20. The current is measurable at the proximal ends 14 which are conveniently outside the vasculature.

The preferred oxygen sensor is preferably carried in a protective sheath (not shown) having an overall diameter suitable for insertion through a catheter, for example, of 20 gauge, that is sized to be inserted into a port of the vasculature of a human or animal. In FIG. 4, the stripped cathode 20 has a shorter length than the length of the stripped anode 21. As shown in FIG. 4 the elongate anode is supported generally parallel to the cathode 20 and near the transition between the stripped portion 21 and the insulated part of the anode is folded into a "U" shape 22 such that the distal end surface 13 thereof faces the distal end surface 13 of the cathode 21. While the figures show the insulation extends along anode 21 beyond the "U" shaped fold 22, that is not required so long as the distal end surface 13 of anode 21 is closer to the distal end surface 13 of cathode 20 as shown in FIG. 4.

We claim:

1. An electrochemical sensor for the determination of the partial pressure of oxygen in a blood stream comprising a cathode and an anode immersed in an electrolyte contained in a chamber defined by an oxygen gas permeable membrane, wherein each of the cathode and anode comprises an exposed, uninsulated distal portion of an elongate insulated conductor having an exposed uninsulated distal end surface and a proximal end; the elongate insulated conductors being associated with a support which positions each conductor with the insulated portion in parallel; and wherein the insulated portion of each conductor has an additional layer of insulation applied over the original insulation.

2. A sensor according to claim 1, in which the additional layer of insulation is applied over the original insulation by co-extrusion.

3. A sensor according to claim 2, in which the additional layer of insulation is made from a polyester or polyethylene.

4. A sensor according to claim 3, in which the cathode is made from silver and the anode is made from silver or silver chloride.

5. A sensor according to claim 1, in which the electrolyte is a buffered potassium chloride solution.

6. An electrical circuit for the in vivo monitoring of the partial pressure of oxygen in a patient's blood stream which comprises, in combination, an electrochemical sensor according to claim 1 connected, through the proximal end of each of the conductors, to a current sensitive measuring device in circuit with a power source, whereby changes in the flow of electric current between the distal end surfaces of the conductors may be monitored.

7. A circuit according to claim 6, in which the additional layer of insulation on each conductor extends up to the proximal end of the conductor.

* * * * *